(12) United States Patent
Brockschmidt et al.

(10) Patent No.: US 10,087,198 B2
(45) Date of Patent: Oct. 2, 2018

(54) REACTION ACCELERATOR FOR A COPOLYMERISATION, ELECTRICAL-INSULATION TAPE, ELECTRICAL-INSULATION BODY, AND CONSOLIDATION BODY

(71) Applicant: Siemens Aktiengesellschaft, Munich (DE)

(72) Inventors: Mario Brockschmidt, Essen (DE); Friedhelm Pohlmann, Essen (DE); Frank Rainer, Oberhausen (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 14/763,790

(22) PCT Filed: Jan. 23, 2014

(86) PCT No.: PCT/EP2014/051330
§ 371 (c)(1),
(2) Date: Jul. 27, 2015

(87) PCT Pub. No.: WO2014/118077
PCT Pub. Date: Aug. 7, 2014

(65) Prior Publication Data
US 2015/0361103 A1 Dec. 17, 2015

(30) Foreign Application Priority Data

Feb. 4, 2013 (EP) ..................... 13153860

(51) Int. Cl.
| | | |
|---|---|---|
| *H01B 3/04* | (2006.01) | |
| *C07F 3/06* | (2006.01) | |
| *C08G 59/42* | (2006.01) | |
| *C08G 59/68* | (2006.01) | |
| *H01B 3/40* | (2006.01) | |
| *C08G 59/02* | (2006.01) | |
| *H01B 3/10* | (2006.01) | |

(52) U.S. Cl.
CPC ............... *C07F 3/06* (2013.01); *C08G 59/02* (2013.01); *C08G 59/42* (2013.01); *C08G 59/681* (2013.01); *H01B 3/04* (2013.01); *H01B 3/10* (2013.01); *H01B 3/40* (2013.01)

(58) Field of Classification Search
CPC ...... C08G 59/02; C08G 59/42; C08G 59/681; H01B 3/04; H01B 3/10; H01B 3/40
USPC ................. 523/218, 400, 457, 466
See application file for complete search history.

(56) References Cited

U.S. PATENT DOCUMENTS

| | | |
|---|---|---|
| 3,449,641 A | 6/1969 | Lee |
| 4,178,274 A | 12/1979 | Denk et al. |
| 4,192,786 A | 3/1980 | Shibayama et al. |
| 4,212,960 A | 7/1980 | Hayashi et al. |
| 4,670,534 A | 6/1987 | Ando et al. |
| 5,030,730 A | 7/1991 | Munk |
| 5,262,491 A | 11/1993 | Jain et al. |
| 6,190,775 B1 | 2/2001 | Smith et al. |
| 8,314,342 B2 | 11/2012 | Ikeda et al. |
| 2014/0138008 A1* | 5/2014 | Groppel ................. B82Y 30/00 156/53 |
| 2015/0361103 A1 | 12/2015 | Brockschmidt et al. |

FOREIGN PATENT DOCUMENTS

| | | |
|---|---|---|
| CN | 86102650 A | 10/1986 |
| CN | 101533788 A | 9/2009 |
| EP | 0198185 A | 10/1986 |
| EP | 0198195 A2 | 10/1986 |
| EP | 0421337 A1 | 4/1991 |
| EP | 1850460 A2 | 10/2007 |
| EP | 2248855 A1 | 11/2010 |
| GB | 2019778 A | 11/1979 |
| GB | 1557960 A | 12/1979 |
| JP | S49105900 A | 10/1974 |
| JP | S5429398 A | 3/1979 |
| JP | S5465759 A | 5/1979 |
| JP | S6026426 A | 2/1985 |
| JP | S6026441 A | 2/1985 |
| JP | H01215821 A | 8/1989 |
| JP | H04502176 A | 4/1992 |
| JP | H0597971 A | 4/1993 |
| JP | 2006057017 A | 3/2006 |
| JP | 2009191239 A | 8/2009 |
| RU | 2332736 C1 | 8/2008 |
| SU | 794673 A1 | 1/1981 |
| WO | 9105015 A1 | 4/1991 |
| WO | 2006009564 A1 | 1/2006 |

(Continued)

OTHER PUBLICATIONS

Hu Zhaobin: "Insulation Material Technology"; Chemistry Industry Press; p. 55; 2005 (in Chinese language).
Li Zidong et al.: "Modern Adhering Technology Manual"; New Age Press; pp. 88-91; 2002 (in Chinese language).
EP Search Report dated Dec. 5, 2016, for EP patent application No. 14702779.1.
JP Decision of Rejection dated Nov. 14, 2016, for JP patent application No. 2015-555657.
Pub Chem Open Chemistry Database, U.S. National Library of Medicine, National Center for Biotechnology Information, "Zinc Octanoate", three pgs, Mar. 16, 2015.

(Continued)

*Primary Examiner* — Edward J Cain

(74) *Attorney, Agent, or Firm* — Beusse Wolter Sanks & Maire

(57) ABSTRACT

A compound having the structural formula $R^1CO_2^- R^2CO_2^- Zn^{2+}$ used as a reaction accelerator for the copolymerization of a mixture of a carboxylic acid anhydride and an oxirane, wherein $R^1$ and $R^2$ are a straight-chained or branched alkyl group independently of each other.

14 Claims, No Drawings

(56) References Cited

FOREIGN PATENT DOCUMENTS

WO      2014118077 A2     8/2014

OTHER PUBLICATIONS

JP Office Action dated Aug. 29, 2016, for JP application No. 2015555657.
CN Decision on Rejection dated Aug. 2, 2017, for CN patent application No. 201480007374.4.
Hu Zhaobin: "Insulation Material Technology"; Chemistry Industry Press; p. 55; 2005.
Li Zidong et al.: "Modern Adhering Technology Manual"; New Age Press; pp. 88-91; 2002.
CN Office Action dated Feb. 14, 2017, for CN patent application No. 201480007374.4.
Handbook of Electrical and Electronic Insulating Technology, Editing Committee of Handbook of Electrical and Electronic Insulating Technology, Mechanical Industry Press; ISBN 978-8-111-22570-6, pp. 1008-1009, Dec. 31, 2007 (English translation).
Russian Federal Office Action dated Nov. 24, 2017, for RU patent application No. 2015132443.

\* cited by examiner

REACTION ACCELERATOR FOR A COPOLYMERISATION, ELECTRICAL-INSULATION TAPE, ELECTRICAL-INSULATION BODY, AND CONSOLIDATION BODY

CROSS REFERENCE TO RELATED APPLICATIONS

This application is the US National Stage of International Application No. PCT/EP2014/051330 filed Jan. 23, 2014, and claims the benefit thereof. The International Application claims the benefit of European Application No. EP13153860 filed Feb. 4, 2013. All of the applications are incorporated by reference herein in their entirety.

FIELD OF INVENTION

The invention relates to a reaction accelerator for a copolymerization, to an electrical insulation tape comprising the reaction accelerator, to an electrical insulation body comprising the electrical insulation tape, and to a consolidation body comprising the reaction accelerator.

BACKGROUND OF INVENTION

Electrical machines, for example motors and generators, include electrical conductors, a main insulation and a laminated stator core. The main insulation has the purpose of electrically insulating the conductors from one another, from the laminated stator core and from the environment. In the region of the electrical machine, partial electrical discharges can form sparks, which can develop what are called "treeing" channels in the main insulation. As a result of the "treeing" channels, there may be electrical sparkover through the main insulation. A barrier against a partial discharges is achieved by the use of mica in the main insulation, the latter having a high partial discharge resistance. The mica is used in the form of mica particles in platelet form having a conventional particle size of several hundreds of micrometers up to several millimeters, the mica particles being processed to give a mica paper. To increase the strength and to increase the processibility, an electrical insulation tape having a support structure as well as the mica paper is used.

To produce the main insulation, the electrical insulation tape is wound around the conductor and then impregnated with a synthetic resin. The synthetic resin is cured in the presence of a reaction accelerator, conventionally zinc naphthenate, i.e. zinc salts of a mixture of cyclopentanoic acids and cyclohexanoic acids. The mixture is obtained in the distillation of crude oil within a particular temperature range, which may have the effect that, starting from different batches of crude oil, the mixture may also be of different composition from batch to batch. As a result, the curing characteristics of the synthetic resin may likewise vary from batch to batch. It is therefore necessary to prepare each batch of the zinc naphthenate in a complex manner, for example by adjusting its pH, its acid number and its viscosity.

EP 0 198 195 A2 describes zinc octylate as reaction accelerator. U.S. Pat. No. 4,178,274 A describes zinc 2-ethylhexanoate as reaction accelerator. U.S. Pat. No. 3,449,641 A discloses zinc octoate in the presence of an epoxy resin. GB 1 557 641 A describes zinc 2-ethylhexanoate in the presence of an epoxy resin. U.S. Pat. No. 6,190,775 B1 describes a flexible insulation tape. GB 2 019 778 A discloses an impregnated mica film. EP 1 850 460 A2 discloses zinc naphthenate in the presence of an epoxy resin.

SUMMARY OF INVENTION

It is an object of the invention to provide a reaction accelerator for a copolymerization, an electrical insulation tape comprising the reaction accelerator, an electrical insulation body comprising the electrical insulation tape and a consolidation body comprising the reaction accelerator, wherein the reaction accelerator is obtainable in a uniform quality.

According to aspects of the invention, a compound having the structural formula $R^1CO_2^-\ R^2CO_2^-\ Zn^{2+}$ is used as a reaction accelerator for the copolymerization of a mixture of a carboxylic anhydride and an oxirane, where $R^1$ and $R^2$ are each independently a straight-chain or branched alkyl group. The electrical insulation tape of the invention, preferably an electrical insulation tape including mica and/or aluminum oxide, includes a compound having the structural formula $R^1CO_2^-\ R^2CO_2^-\ Zn^{2+}$ where $R^1$ and $R^2$ are each a straight-chain or branched alkyl group. The electrical insulation body of the invention for an electrical conductor includes the electrical insulation tape of the invention, wherein the mixture of the carboxylic anhydride and the oxirane is cured in the presence of the compound having the structural formula $R^1CO_2^-\ R^2CO_2^-\ Zn^{2+}$ where $R^1$ and $R^2$ are each a straight-chain or branched alkyl group.

The consolidation body of the invention for an end winding for a rotating electrical machine includes a porous and electrically nonconductive main body including a compound having the structural formula $R^1CO_2^-\ R^2CO_2^-\ Zn^{2+}$ and has been impregnated by a mixture of a carboxylic anhydride and an oxirane cured in the presence of a compound having the structural formula $R^1CO_2^-\ R^2CO_2^-\ Zn^{2+}$ where $R^1$ and $R^2$ are each a straight-chain or branched alkyl group.

The compound having the structural formula $R^1CO_2^-\ R^2CO_2^-\ Zn^{2+}$ is commercially available with a uniform quality and/or preparable with a uniform quality. It is thus ensured in an advantageous manner that the use of the compound as reaction accelerator results in essentially identical copolymerization of the mixture from batch to batch. In addition, the electrical insulation tape including the compound, by virtue of the uniform quality of the compound, likewise has uniform impregnation characteristics, as a result of which it is advantageously possible for the mixture to impregnate the electrical insulation tape in uniform quality. As a result of the copolymerization proceeding in an identical manner and the uniform impregnation of the electrical insulation tape, it is advantageously possible to produce the electrical insulation body and the consolidation body with a homogeneous quality.

The electrical insulation body may be provided, for example, as a main insulation for an electrical generator. It is also conceivable that the main insulation is provided in the region of the end windings of the electrical generator.

If aluminum oxide is used in place of or as well as the mica, the result is a higher thermal conductivity of the main insulation, as a result of which it is possible to keep the temperature of the main insulation low, and hence its lifetime is advantageously long.

Preferably, $R^1$ and $R^2$ are each independently $C_6$alkyl, $C_7$alkyl, $C_8$alkyl, $C_9$alkyl or $C_{10}$alkyl. It is surprisingly possible for the mixture to more quickly and uniformly impregnate the electrical insulation tape including the reaction accelerator having these alkyl groups than is the case with zinc naphthenate, as a result of which a homogeneous electrical insulation body advantageously forms after the curing of the mixture of the carboxylic anhydride and the oxirane. The same applies to the consolidation body.

$R^1$ and $R^2$ are preferably each independently n-heptyl, 1-methyl-n-hexyl, 2-methyl-n-hexyl, 3-methyl-n-hexyl, 4-methyl-n-hexyl, 5-methyl-n-hexyl, 3-ethyl-n-pentyl, 2-ethyl-n-pentyl, 1-ethyl-n-pentyl, 1,1-dimethyl-n-pentyl, 2,2-dimethyl-n-pentyl, 3,3-dimethyl-n-pentyl, 4,4-dimethyl-n-pentyl, 1,2-dimethyl-n-pentyl, 1,3-dimethyl-n-pentyl, 1,4-dimethyl-n-pentyl, 2,3-dimethyl-n-pentyl, 2,4-dimethyl-n-pentyl, 3,4-dimethyl-n-pentyl, 1,1,2-trimethyl-n-butyl, 1,1,3-trimethyl-n-butyl, 1,2,3-trimethyl-n-butyl, 1,2,2-trimethyl-n-butyl, 2,2,3-trimethyl-n-butyl, 2,3,3-trimethyl-n-butyl, 1,3,3-trimethyl-n-butyl, 1-ethyl-1-methyl-n-butyl, 1-ethyl-2-methyl-n-butyl, 1-ethyl-3-methyl-n-butyl, 2-ethyl-1-methyl-n-butyl, 2-ethyl-2-methyl-n-butyl, 2-ethyl-3-methyl-n-butyl, 1-isopropyl-n-butyl, 2-isopropyl-n-butyl, 1,1,2,2-tetramethyl-n-propyl, 1,1-diethyl-n-propyl, 2,2-dimethyl-1-ethyl-n-propyl, 1,2-dimethyl-1-ethyl-n-propyl, 1-isopropyl-1-methyl-n-propyl or 1-isopropyl-2-methyl-n-propyl or neononyl, preferably a tertiary $C_9$alkyl group, more preferably 1,1-dimethyl-n-heptyl, 1,1,2-trimethyl-n-hexyl, 1,1,3-trimethyl-n-hexyl, 1,1,4-trimethyl-n-hexyl, 1,1,5-trimethyl-n-hexyl, 1-ethyl-1-methyl-n-hexyl, 1,2-dimethyl-1-ethyl-n-pentyl, 1,3-dimethyl-1-ethyl-n-pentyl, 1,4-dimethyl-1-ethyl-n-pentyl, 1,1-dimethyl-2-ethyl-n-pentyl, 1,1-dimethyl-3-ethyl-n-pentyl, 1,1,2,2-tetramethyl-n-pentyl, 1,1,2,3-tetramethyl-n-pentyl, 1,1,2,4-tetramethyl-n-pentyl, 1,1,3,3-tetramethyl-n-pentyl, 1,1,3,4-tetramethyl-n-pentyl, 1,1,4,4-tetramethyl-n-pentyl, 1,1-diethyl-n-pentyl, 1-methyl-1-n-propyl-n-pentyl, 1-methyl-1-isopropyl-n-pentyl, 1,1,2,2,3-pentamethyl-n-butyl, 1,1,2,3,3-pentamethyl-n-butyl, 1-ethyl-1,2,2-trimethyl-n-butyl, 1-ethyl-1,2,3-trimethyl-n-butyl, 1-ethyl-1,3,3-trimethyl-n-butyl, 2-ethyl-1,1,2-trimethyl-n-butyl, 2-ethyl-1,1,3-trimethyl-n-butyl, 1,2-dimethyl-1-n-propyl-n-butyl, 1,3-dimethyl-1-n-propyl-n-butyl, 1-ethyl-1-n-propyl-n-butyl, 1,2-dimethyl-1-isopropyl-n-butyl, 1,3-dimethyl-1-isopropyl-n-butyl, 1-ethyl-1-isopropyl-n-butyl, 1,1-diethyl-2-methyl-n-butyl, 1,1-diethyl-3-methyl-n-butyl, 1,2-diethyl-1-methyl-n-butyl, 1-methyl-1-tert-butyl-n-butyl, 1,1-diethyl-2,2-dimethyl-n-propyl, 1-isopropyl-1,2,2-trimethyl-n-propyl, 1,1-diisopropyl-n-propyl, or 6,6-dimethyl-n-heptyl.

These compounds include, for example, zinc octanoate and zinc neodecanoate, which are commercially available, for example, from OMG Borchers, Germany, under the trade names Borchikat 15, Borchikat 22, Soligen Zinc 11/12, Octa-Soligen-Zinc 22, in a high purity compared to zinc naphthenate.

The carboxylic anhydride is preferably a cyclic carboxylic anhydride, especially phthalic anhydride, methylhexahydrophthalic anhydride and/or hexahydrophthalic anhydride. The oxirane is preferably a bisoxirane, especially bisphenol A diglycidyl ether and/or bisphenol F diglycidyl ether. It is preferably styrene, preferably with a proportion by mass of 0% to about 60%, based on the mixture. Particular preference is given to about 3% to about 10% styrene. The reactive diluent advantageously lowers the viscosity of the mixture for better impregnatability of the electrical insulation tape and/or the consolidation body and is converted in the copolymerization as well.

The electrical insulation tape has preferably been impregnated by a mixture of a carboxylic anhydride and an oxirane.

Preferably, the electrical insulation body includes partial discharge-resistant nanoscale particles, preferably with a proportion by mass of the particles of 2% to 10%, based on the mixture of the carboxylic anhydride, the oxirane and the particles. As a result, the partial discharge resistance of the electrical insulation body increases, which advantageously prolongs its lifetime. It is preferable that the particles are inorganic particles, especially particles including silicon dioxide, titanium dioxide and/or aluminum oxide. Preferably, the mean particle diameter of the particles is between 1 nm and 50 nm. For production of the electrical insulation body, the particles are added to the mixture of the carboxylic anhydride and the oxirane prior to the impregnation of the electrical insulation tape. Through a silanization of the surfaces of the particles by reacting the particles with alkylalkoxysilanes, especially methyl-trimethoxysilane, dimethyldimethoxysilane and/or trimethylmethoxysilane, it is possible to organophilize the surface of the particles, such that the particles are advantageously better miscible with the mixture of the carboxylic anhydride and the oxirane, without any unwanted agglomeration of the particles. However, the particles in the mixture likewise accelerate the copolymerization. In the case that nanoparticles are present in the mixture, it is essential for homogeneous formation of the electrical insulation body to provide the reaction accelerator in the electrical insulation tape.

Preferably, the electrical insulation tape has a porous and electrically nonconductive support structure, especially a knit, a nonwoven fabric, a foam, especially an open-pore form, a glass knit, a glass roving, a woven fabric and/or a resin mat. The porosity of the support structure is such that it can be impregnated by the mixture. The support structure preferably includes a polyester, especially Dacron, and/or polyethylene terephthalate (PET). The support structure has preferably been bonded with an insulation paper, especially an insulation paper including mica and/or aluminum oxide. The insulation paper preferably has such a porosity that it can be impregnated by the mixture.

The main body of the consolidation body preferably includes a knit, a nonwoven fabric, a foam, especially an open-pore form, a glass knit, a glass roving, a woven fabric and/or a resin mat. Preferably, the consolidation body is provided in the region of the end winding of an electrical machine, especially of a motor or generator, and between the electrical conductors of the end winding. Preferably, the consolidation body is arranged in the region of the end winding so as to bring about stiffening of the end winding, such that the end winding becomes less sensitive to induced vibration in the region of the electrical machine and hence has a long lifetime. In the production of the consolidation body, it can be impregnated by the mixture of the carboxylic anhydride and the oxirane simultaneously with the electrical insulation body. Preferably, the main body of the consolidation body includes a polyester, especially Dacron, and/or polyethylene terephthalate (PET).

DETAILED DESCRIPTION OF INVENTION

The invention is elucidated in detail hereinafter by four examples.

In a first example, the electrical insulation body is produced as follows: a porous and hence impregnatables electrical insulation tape including mica paper is impregnated with a solution of zinc neodecanoate in a solvent, especially naphtha. Possible alternatives to impregnation are roll application, spraying, dipping, trickling, a point-to-point method and/or a kiss-coating method. Subsequently, the solvent is removed from the electrical insulation tape, especially by supplying heat and/or by vacuum drying. The electrical insulation tape is wound around an electrical conductor. The electrical conductor, preferably with such a winding, is introduced into a bath of a stoichiometric mixture of bisphenol A diglycidyl ether and hexahydrophthalic anhydride. The electrical insulation tape and cavities between individual windings of the electrical insulation tape are impregnated by the mixture in the bath in a VPI (vacuum pressure impregnation) process with application of a vacuum. Subsequently, the mixture is cured in the VPI process by application of pressure, and hence the electrical insulation body is completed.

In a second example, the electrical insulation body is produced as follows: a porous mica paper is bonded by means of an adhesive to a porous resin mat made from PET, and an electrical insulation tape is thus produced. A solution of zinc n-octanoate in naphtha is sprayed onto the electrical insulation tape, and then the naphtha is removed from the electrical insulation tape by means of vacuum drying. The electrical insulation tape is wound around an electrical conductor and the electrical conductor, preferably with such a winding, is introduced into a bath of a stoichiometric mixture of bisphenol F diglycidyl ether and methylhexahydrophthalic anhydride. To reduce the viscosity of the mixture, the mixture likewise includes 10 percent by mass of styrene, based on the mixture. The electrical insulation tape and cavities between individual windings of the electrical insulation tape are impregnated by the mixture in the bath in a VPI process with application of a vacuum. Subsequently, the mixture is cured in the VPI process by application of pressure, and hence the electrical insulation body is completed.

In a third example, the electrical insulation paper is produced as follows: a porous mica paper is bonded to a glass knit by means of an adhesive, and an electrical insulation tape is thus produced. The electrical insulation tape is impregnated with a solution of zinc n-octanoate in naphtha, and then the naphtha is removed from the electrical insulation tape by supplying heat. The electrical insulation tape is wound around an electrical conductor, and the electrical conductor with such a winding is introduced into a bath of a stoichiometric mixture of bisphenol F diglycidyl ether and methylhexahydrophthalic anhydride. The mixture likewise includes particles of titanium dioxide having a mean particle diameter of 50 nm and a proportion of 3 percent by mass, based on the mixture. To reduce the viscosity of the mixture, the mixture also includes 10 percent by mass of styrene, based on the mixture. The electrical insulation tape and cavities between individual windings of the electrical insulation tape are impregnated by the mixture in the bath in a VPI process with application of a vacuum. Subsequently, the mixture is cured in the VPI process by application of pressure, and hence the electrical insulation body is completed.

In a fourth example, the consolidation body is produced as follows: a porous and hence impregnatable woven fabric made from PET is impregnated with a solution of zinc neodecanoate in a solvent, especially naphtha. Subsequently, the solvent is removed from the woven fabric by vacuum drying. The woven fabric is subsequently wound around the end winding of an electrical machine. The electrical machine together with the end winding is introduced into a bath of a stoichiometric mixture of bisphenol A diglycidyl ether and hexahydrophthalic anhydride. The woven fabric is impregnated by the mixture in the bath in a VPI process with application of a vacuum. Subsequently, the mixture is cured in the VPI process by application of pressure, and hence the electrical insulation body is completed. The consolidation body thus completed brings about stiffening of the end winding, such that it has less of a tendency to vibrate in the course of operation of the electrical machine.

Even though the invention has been illustrated and described in detail by the preferred working examples, the invention is not restricted by the examples disclosed, and other variations may be derived therefrom by the person skilled in the art without leaving the scope of protection of the invention.

The invention claimed is:

1. An electrical insulation tape, comprising
a compound having the structural formula $R1CO2-R2CO2-Zn2+$,
where R1 and R2 are each independently a straight-chain or branched alkyl group, where R1 and R2 are each independently
n-heptyl, 1-methyl-n-hexyl, 2-methyl-n-hexyl, 3-methyl-n-hexyl, 4-methyl-n-hexyl, 5-methyl-n-hexyl, 3-ethyl-n-pentyl, 2-ethyl-n-pentyl, 1,1-dimethyl-n-pentyl, 2,2-dimethyl-n-pentyl, 3,3-dimethyl-n-pentyl, 4,4-dimethyl-n-pentyl, 1,2-dimethyl-n-pentyl, 1,3-dimethyl-n-pentyl, 1,4-dimethyl-n-pentyl, 2,3-dimethyl-n-pentyl, 2,4-dimethyl-n-pentyl, 3,4-dimethyl-n-pentyl, 1,1,2-trimethyl-n-butyl, 1,1,3-trimethyl-n-butyl, 1,2,3-trimethyl-n-butyl, 1,2,2-trimethyl-n-butyl, 2,2,3-trimethyl-n-butyl, 2,3,3-trimethyl-n-butyl, 1,3,3-trimethyl-n-butyl, 1-ethyl-1-methyl-n-butyl, 1-ethyl-2-methyl-n-butyl, 1-ethyl-3-methyl-n-butyl, 2-ethyl-1-methyl-n-butyl, 2-ethyl-2-methyl-n-butyl, 2-ethyl-3-methyl-n-butyl, 1-isopropyl-n-butyl, 2-isopropyl-n-butyl, 1,1,2,2-tetramethyl-n-propyl, 1,1-diethyl-n-propyl, 2,2-dimethyl-1-ethyl-n-propyl, 1,2-dimethyl-1-ethyl-n-propyl, 1-isopropyl-1-methyl-n-propyl or 1-isopropyl-2-methyl-n-propyl,
C6alkyl, C8alkyl, C9alkyl or C10alkyl,
wherein the electrical insulation tape has been impregnated by a mixture of a carboxylic anhydride and an oxirane, and
wherein the mixture of the carboxylic anhydride and the oxirane comprises a reactive diluent comprising styrene with a proportion by mass of about 3% to about 10%, based on the mixture.

2. An electrical insulation body for an electrical conductor, wherein the electrical insulation body comprises:
an electrical insulation tape as claimed in claim 1,
wherein the mixture of the carboxylic anhydride of the oxirane has been cured in the presence of the compound having the structural formula $R1CO2-R2CO2-Zn2+$.

3. The electrical insulation body as claimed in claim 2, wherein the electrical insulation body includes partial discharge-resistant nanoscale particles.

4. A consolidation body for an end winding of a rotating electrical machine, wherein the consolidation body comprises:
a porous and electrically nonconductive main body including a compound having the structural formula $R1CO2-R2CO2-Zn2+$ and has been impregnated by a mixture of a carboxylic anhydride and in oxirane which has been cured in the presence of the compound having the structural formula $R1CO2-R2CO2-Zn2+$,
where R1 and R2 are each independently a straight-chain or branched alkyl group, where R1 and R2 are each independently
n-heptyl, 1-methyl-n-hexyl, 2-methyl-n-hexyl, 3-methyl-n-hexyl, 4-methyl-n-hexyl, 5-methyl-n-hexyl, 3-ethyl-n-pentyl, 2-ethyl-n-pentyl, 1,1-dimethyl-n-pentyl, 2,2-dimethyl-n-pentyl, 3,3-dimethyl-n-pentyl, 4,4- dimethyl-n-pentyl, 1,2-dimethyl-n-pentyl, 1,3-dimethyl-n-pentyl, 1,4-dimethyl-n-pentyl, 2,3-dimethyl-n-pentyl, 2,4-dimethyl-n-pentyl, 3,4-dimethyl-n-pentyl, 1,1,2-trimethyl-n-butyl, 1,1,3-trimethyl-n-butyl, 1,2,3-trimethyl-n-butyl, 1,2,2-trimethyl-n-butyl, 2,2,3-trimethyl-n-butyl, 2,3,3-trimethyl-n-butyl, 1,3,3-trimethyl-n-butyl, 1-ethyl-1-methyl-n-butyl, 1-ethyl-2-methyl-n-butyl, 1-ethyl-3-methyl-n-butyl, 2-ethyl-1-methyl-n-butyl, 2-ethyl-2-methyl-n-butyl, 2-ethyl-3-methyl-n-butyl, 1-isopropyl-n-butyl, 2-isopropyl-n-butyl, 1,1,2,2-tetramethyl-n-propyl, 1,1-diethyl-n-propyl, 2,2-dimethyl-1-ethyl-n-propyl, 1,2-dimethyl-1-ethyl-n-propyl, 1-isopropyl-1-methyl-n-propyl or 1-isopropyl-2-methyl-n-propyl, C6alkyl, C8alkyl, C9alkyl or C10alkyl, wherein the mixture of the carboxylic anhydride and the oxirane comprises a reactive diluent comprising styrene with a proportion by mass of about 3% to about 10%, based on the mixture.

5. The electrical insulation body as claimed in claim 2, wherein the electrical insulation body includes partial discharge-resistant nanoscale particles having a proportion by mass of the particles of 2% to 10%, based on the mixture of the carboxylic anhydride, the oxirane and the particles.

6. The electrical insulation tape as claimed in claim 1, wherein the electrical insulation tape comprises mica and/or aluminum oxide.

7. The electrical insulation tape of claim 1, wherein the carboxylic anhydride comprises a cyclic carboxylic anhydride.

8. The electrical insulation tape of claim 7, wherein the cyclic carboxylic anhydride comprises at least one of phthalic anhydride, methylhexahydro-phthalic anhydride and hexahydrophthalic anhydride.

9. The electrical insulation tape of claim 1, wherein the oxirane comprises a bisoxirane.

10. The electrical insulation tape of claim 9, wherein the bisoxirane comprises at least one of bisphenol A diglycidyl ether and bisphenol F diglycidyl ether.

11. The consolidation body of claim 4, wherein the carboxylic anhydride comprises a cyclic carboxylic anhydride.

12. The consolidation body of claim 11, wherein the cyclic carboxylic anhydride comprises at least one of phthalic anhydride, methylhexahydro-phthalic anhydride and hexahydrophthalic anhydride.

13. The consolidation body of claim 4, wherein the oxirane comprises a bisoxirane.

14. The consolidation body of claim 13, wherein the bisoxirane comprises at least one of bisphenol A diglycidyl ether and bisphenol F diglycidyl ether.

* * * * *